(12) United States Patent
Cannell et al.

(10) Patent No.: US 9,050,110 B2
(45) Date of Patent: Jun. 9, 2015

(54) MEDICAL DEVICE

(75) Inventors: Matthew Cannell, Rugby (GB); Nicholas Turner, Cheltenham (GB)

(73) Assignee: T. J. Smith & Nephew Limited, Hull (GB)

( * ) Notice: Subject to any disclaimer, the term of this patent is extended or adjusted under 35 U.S.C. 154(b) by 1102 days.

(21) Appl. No.: 13/002,786

(22) PCT Filed: Jul. 7, 2009

(86) PCT No.: PCT/GB2009/001682
§ 371 (c)(1),
(2), (4) Date: Apr. 1, 2011

(87) PCT Pub. No.: WO2010/004267
PCT Pub. Date: Jan. 14, 2010

(65) Prior Publication Data
US 2012/0023733 A1    Feb. 2, 2012

(30) Foreign Application Priority Data
Jul. 7, 2008   (GB) .................................. 0812406.7

(51) Int. Cl.
*B23B 31/103*   (2006.01)
*B25G 3/18*     (2006.01)
*B25G 3/24*     (2006.01)
*A61B 17/16*    (2006.01)

(52) U.S. Cl.
CPC ............. *A61B 17/1617* (2013.01); *B25G 3/18* (2013.01); *B25G 3/24* (2013.01); *B23B 31/103* (2013.01); *A61B 17/162* (2013.01); *A61B 17/1631* (2013.01); *A61B 17/1666* (2013.01)

(58) Field of Classification Search
CPC ........... B23B 31/103; B25G 3/18; B25G 3/24
USPC .............. 29/465; 279/33, 35, 44, 89, 93, 106, 279/138; 403/375, 322.3, 330, 348, 349; 292/210, 213
IPC ......................... B23B 31/103; B25G 3/18, 3/24
See application file for complete search history.

(56) References Cited

U.S. PATENT DOCUMENTS

| 17,655 | A | * | 6/1857 | Richards ...................... 408/215 |
| 609,478 | A | * | 8/1898 | Sturgis ........................ 279/35 |
| 1,187,920 | A | * | 6/1916 | Muller ........................ 82/165 |
| 1,433,590 | A | * | 10/1922 | Ziegler ....................... 279/35 |

(Continued)

FOREIGN PATENT DOCUMENTS

| EP | 1074225 A1 | 2/2001 |
| FR | 2281095 A1 | 3/1976 |

(Continued)

OTHER PUBLICATIONS

European Office Action; European Patent Office; European Patent Application No. 09784647.1; Feb. 11, 2015; 5 pages.

*Primary Examiner* — Eric A Gates
(74) *Attorney, Agent, or Firm* — Krieg DeVault LLP

(57) ABSTRACT

A device (1) for connecting an instrument to a driver, the device comprising: a first connector (3) having at least two protrusions connectable, in use, to the instrument; a mechanism for moving the protrusions between a connected and a disconnected position; and a second connector (17) for connecting the device (1) to the driver, in use. Also disclosed is a method of connecting an instrument to a driver.

24 Claims, 10 Drawing Sheets

(56) References Cited

U.S. PATENT DOCUMENTS

| | | | | |
|---|---|---|---|---|
| 1,494,056 | A * | 5/1924 | Benko | 192/56.5 |
| 1,564,768 | A * | 12/1925 | Emrick | 279/33 |
| 3,596,917 | A * | 8/1971 | Meyer | 279/89 |
| 4,249,799 | A * | 2/1981 | Iglesias | 359/827 |
| 5,203,874 | A * | 4/1993 | Azkona-Ollacarizqueta | 470/82 |
| 5,464,301 | A * | 11/1995 | Kramer | 403/322.3 |
| 5,645,365 | A * | 7/1997 | Malish et al. | 403/348 |
| 6,264,647 | B1 * | 7/2001 | Lechot | 606/1 |
| 7,115,119 | B2 * | 10/2006 | Desarzens | 606/1 |
| 7,473,048 | B2 * | 1/2009 | Nakamura et al. | 403/56 |
| 7,674,064 | B2 * | 3/2010 | Nakamura et al. | 403/348 |
| 7,955,320 | B2 * | 6/2011 | Desarzens et al. | 606/1 |
| 8,323,284 | B2 * | 12/2012 | Ferreira | 606/80 |
| 8,439,920 | B2 * | 5/2013 | Ryall et al. | 606/80 |
| 2007/0225722 | A1 | 9/2007 | Parker | |
| 2011/0060342 | A1 * | 3/2011 | Turner et al. | 606/91 |
| 2011/0118743 | A1 * | 5/2011 | Cannell et al. | 606/80 |
| 2012/0076569 | A1 * | 3/2012 | Ecochard | 403/33 |

FOREIGN PATENT DOCUMENTS

| | | |
|---|---|---|
| WO | WO 2004/100805 A | 11/2004 |
| WO | WO 2005/044114 A | 5/2005 |

* cited by examiner

MEDICAL DEVICE

This application is a United States National Phase filing of International Application No. PCT/GB2009/001682 filed on Jul. 7, 2009 which claims the benefit of GB 0812406.7 filed Jul. 7, 2008, both of which are herein incorporated by reference.

The present invention relates to a device for connecting an instrument to a driver. In particular, the present invention relates to a device for connecting a cutting tool to a driver.

Large orthopaedic instrument kits are not desirable in a surgical environment. In order to reduce the size of instrument kits, the use of modular connections has become commonplace. Before the introduction of modular connections, it was necessary to have a handle fixed to every cutting instrument, thereby significantly increasing the size of the kits. By using a modular connection, a single handle may be interfaced to a full range of instruments. Modular connections are used with a range of rotary instruments, including cutting instruments such as sleeve cutters, chamfer cutters, plane cutters and acetabular reamers.

Two particular designs of modular connection have become standard with rotary instruments, namely the 'crucifix' connection and the 'bridge-back' connection. Known modular connections on driver handles tend to only interface with one of the above types of connection on the mating instrument. Such modular connections have the disadvantage that they are not universally transferable between different types of instrument kits.

Known modular connections use a bayonet means of attachment. This means of attachment does not provide a rigid connection and can adversely affect the performance of the instrument and compromise the integrity of the device.

The present invention overcomes the above problems.

According to a first aspect of the present invention, there is provided a device for connecting an instrument to a driver, the device comprising:
 a first connector having at least two protrusions connectable, in use, to the instrument;
 a mechanism for moving the protrusions between a connected and a disconnected position; and
 a second connector for connecting the device to the driver, in use.

In use, the protrusions of the device may connect to the instrument such that the instrument is clamped by the device.

The mechanism may move the protrusions independently of each other.

The mechanism may move the protrusions in opposite directions.

The mechanism may rotate the protrusions independently of each other.

The mechanism may rotate the protrusions in opposite directions.

At least one protrusion may be shaped so that it engages with a corresponding shape on the instrument.

At least one protrusion may be in the form of a catch. The catch may be tapered.

The instrument may have at least one arm. The protrusions of the device may connect to the at least one arm.

The at least one arm may be circular in cross-section. The at least one arm may be n-sided, where n is 3 or more. The at least one arm may be square in cross-section. The at least one arm may be rectangular in cross-section.

The first connector may be disposed at the distal end of a drive shaft and the second connector may be disposed at the proximal end of the drive shaft.

The instrument may be a cutting tool. The cutting tool may be a reamer. The cutting tool may be a sleeve cutter. The cutting tool may be a chamfer cutter. The cutting tool may be a plane cutter.

The driver may be a rotary drive source. The rotary drive source may be a power drill.

An advantage of devices according to the present invention is that they allow both standard types of modular connection, namely crucifix and bridge-back, to attach to a single device. Devices according to the present invention also allow a plurality of different, non-standard types of modular connection to attach to a single device.

Another advantage of devices according to the present invention is that they provide a more secure connection than known bayonet type devices. This is due to the larger area over which the design supports the modular connection. It is also due to the 'clamping' action resulting from the protrusions.

Embodiments of the present invention provide a driver handle which can securely connect to bridge-back or crucifix modular connections. The instrument maintains a rigid connection, is easy and intuitive to use, and is easy to clean.

According to a preferred embodiment of the present invention, there is provided a device having a main body and a rotating locking ring. Both the main body and locking ring have a cut-out feature that enables either a bridge-back or crucifix connection to be securely held. By rotating the locking ring relative to the main body, the two cut-out features 'meet' creating a recess to hold the modular connection.

In order to secure the assembly and prevent the modular connection from disconnecting with the modular handle, a sliding securing block is also used. The securing block slides along the axis of the modular handle, and locates through mating features in the main body and locking ring in order to prevent the two components from rotating relative to each other.

Reference will now be made, by way of example, to the accompanying drawings in which.

Figure 1:
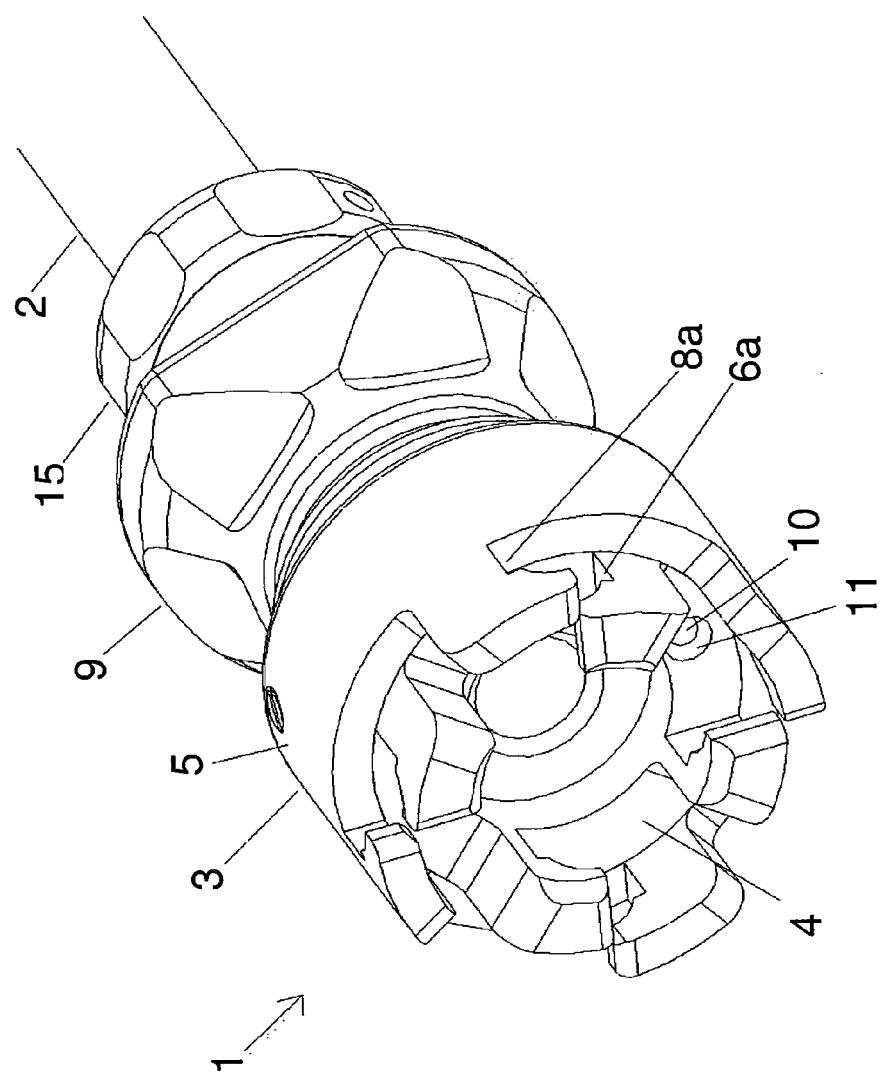
FIG. 1 shows the distal end of a device according to an embodiment of the present invention in the closed position.
Figure 5:
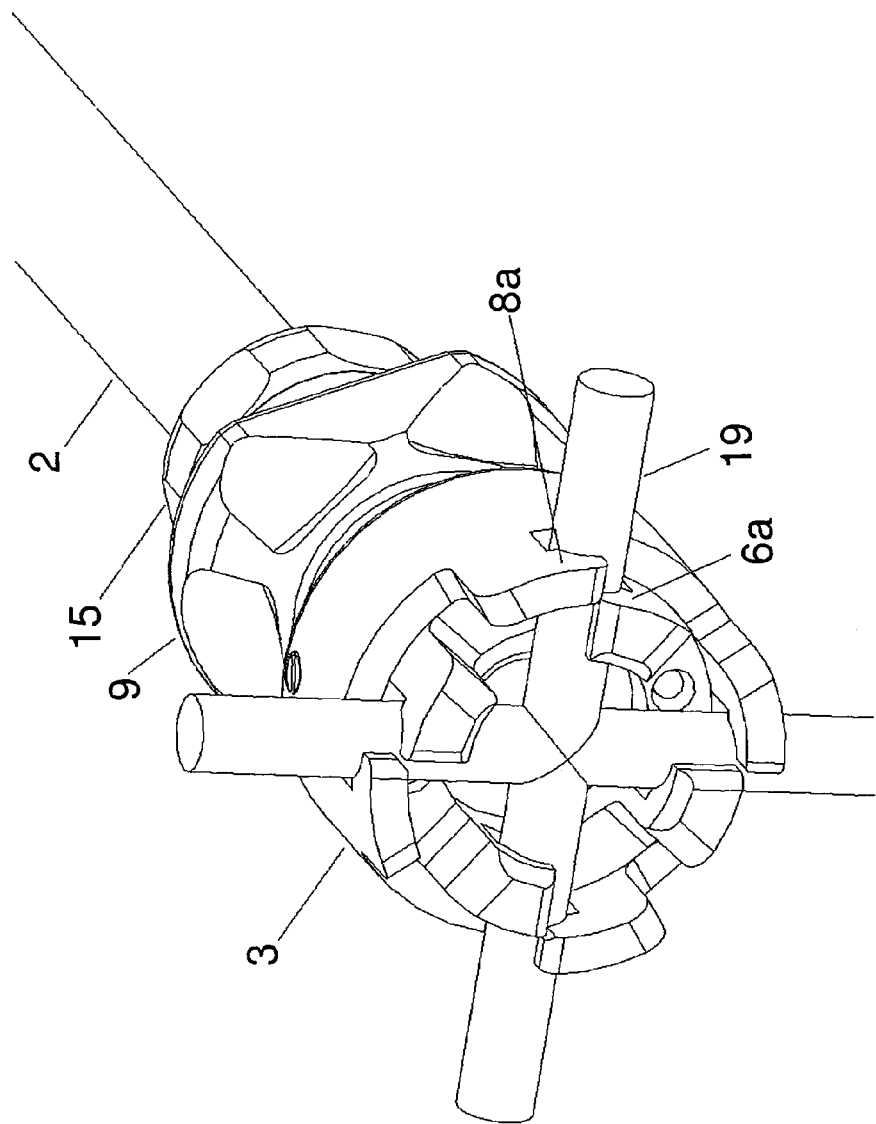
FIG. 5 shows the device of FIG. 1 connected to a crucifix connector.
Figure 6:
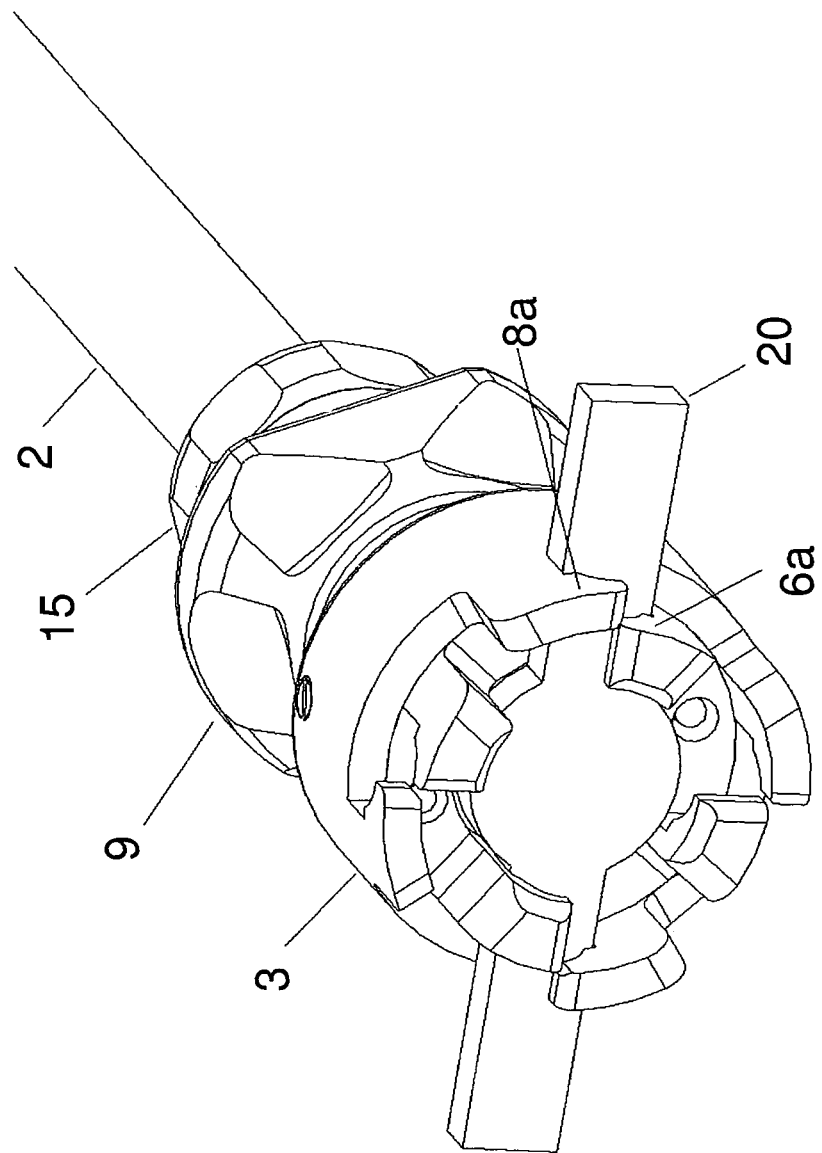
FIG. 6 shows the device of FIG. 1 connected to a bridge-back connector.
Figure 7:
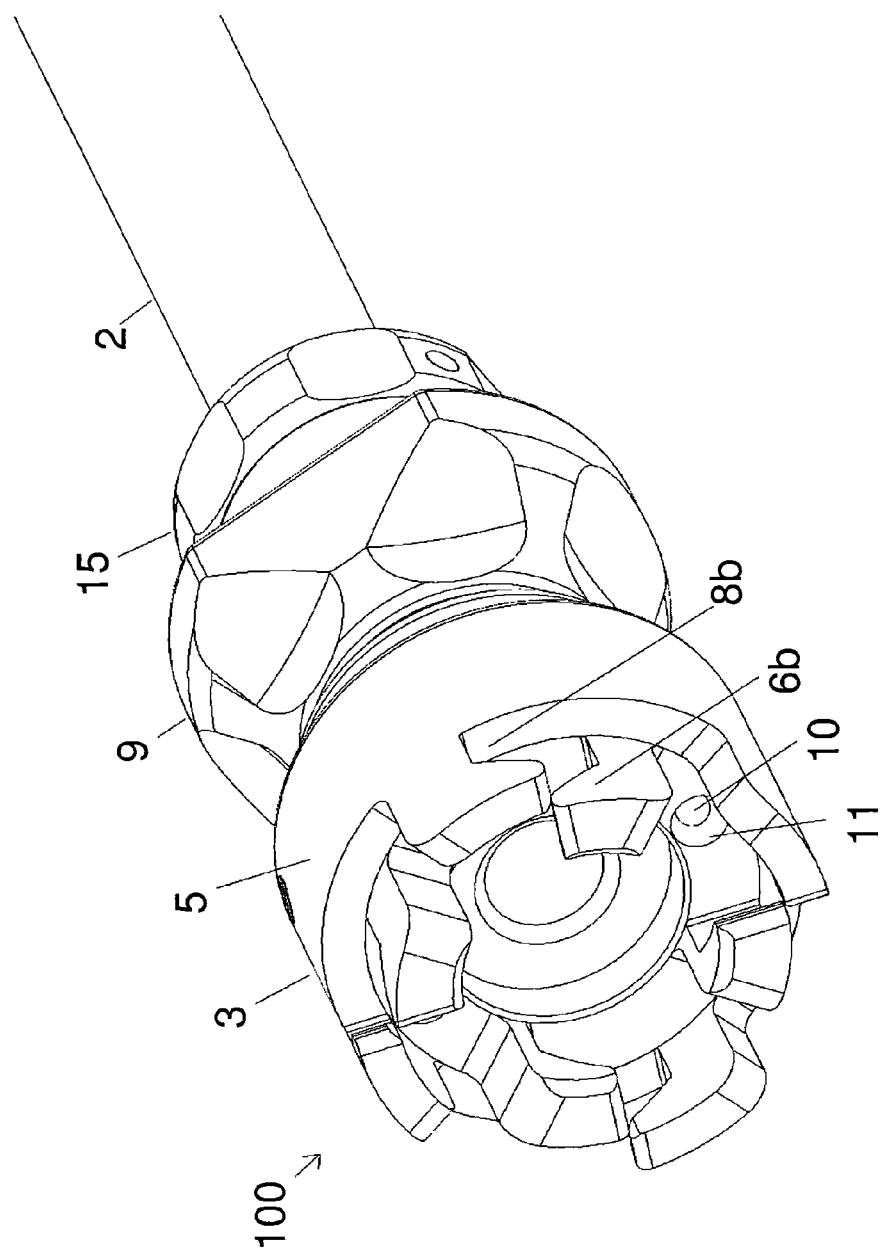
FIG. 7 shows the distal end of a device according to another embodiment of the present invention in the closed position.
Figure 8:
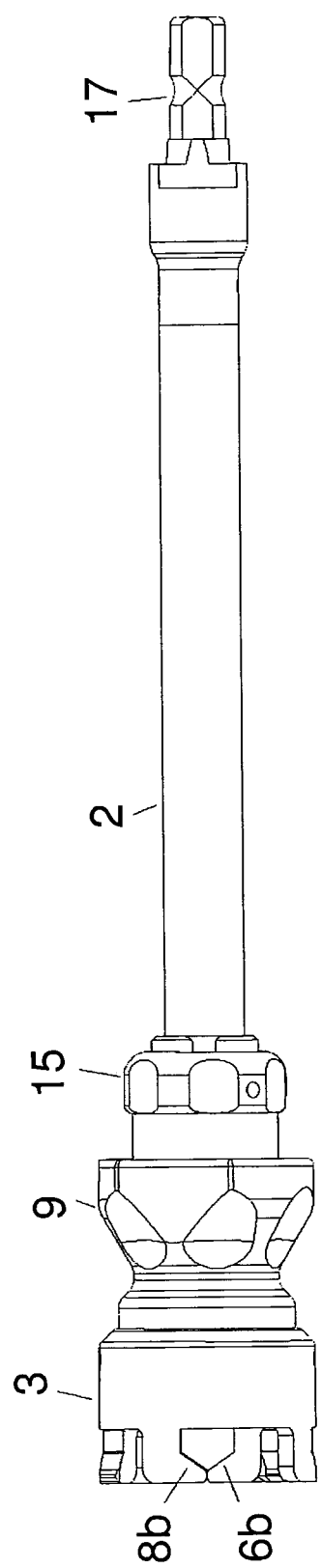
FIG. 8 is a side profile view of the device of FIG. 7.

As shown in FIG. 1, the device 1 comprises a main body 2, having a first connector 3 disposed at its distal end connectable, in use, to at least one arm on a cutting tool. In the embodiment shown, connector 3 comprises two concentric rings 4,5. Inner ring 4 is attached to the distal end of main body 2 and has four protrusions in the form of tapered catches 6a that are equally spaced around the central axis of main body 2. Tapered catches 6a are shaped with a circular and square profile such that they correspond to both the round cross-sectional profile of the crucifix connection 19 (see FIG. 5) and the rectangular profile of the bridge-back connection 20 (see FIG. 6).

Outer ring 5 is slidably mounted on body 2 such that it can be disposed around inner ring 4, when in use. Outer ring 5 has four protrusions in the form of tapered catches 8a that are equally spaced around the central axis of main body 2. Tapered catches 8a are shaped with a circular and square profile such that they correspond to both the round cross-sectional profile of the crucifix connection 19 (see FIG. 5) and the rectangular profile of the bridge-back connection 20 (see FIG. 6). The tapered catches 8a of outer ring 5 are the same as tapered catches 6a of inner ring 4, except that they are oriented in the opposite direction.

Figure 2:
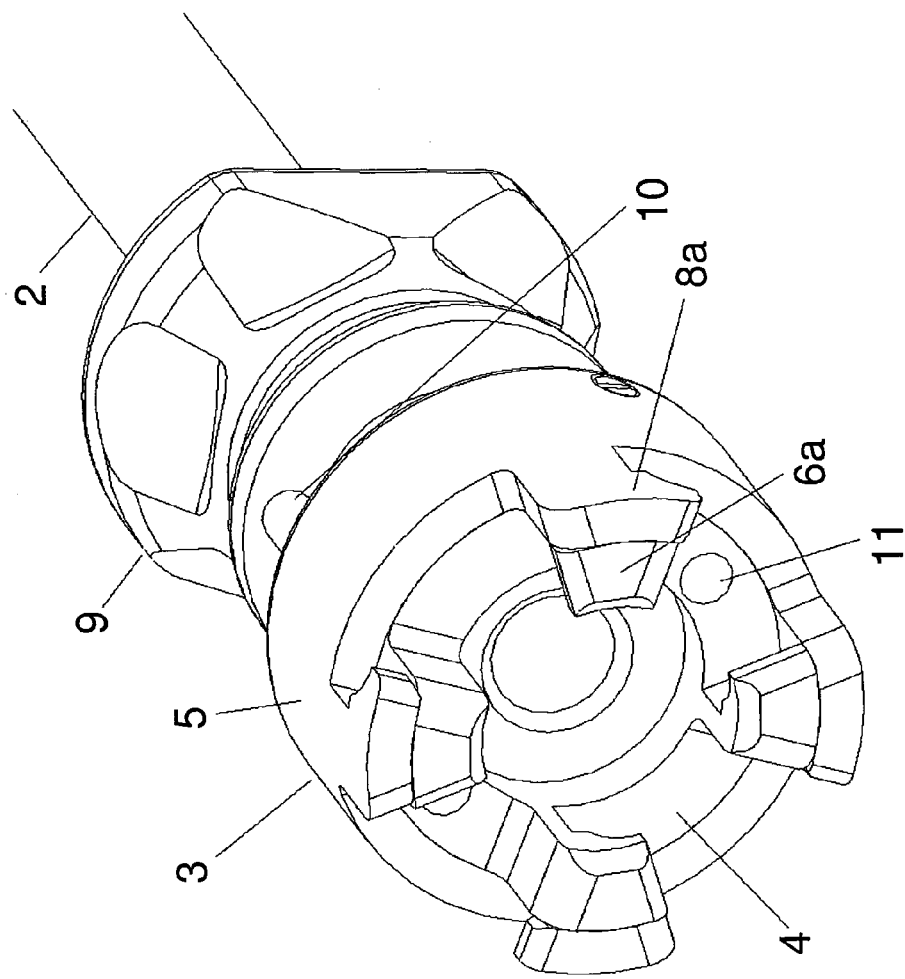
FIG. 2 shows the device of FIG. 1 in the open position.

To secure a cutting tool to the device 1 the outer ring 5 is positioned concentric to the outside of the inner ring 4. When the outer ring 5 is rotated anti-clockwise relative to the inner ring 4, the tapered catches 6a, 8a meet creating a cavity which secures the modular connection (either crucifix or bridge-back) of the cutting tool to the device 1. This is the closed position, as shown in FIG. 1. FIG. 2 shows the corresponding open position.

Figure 4:
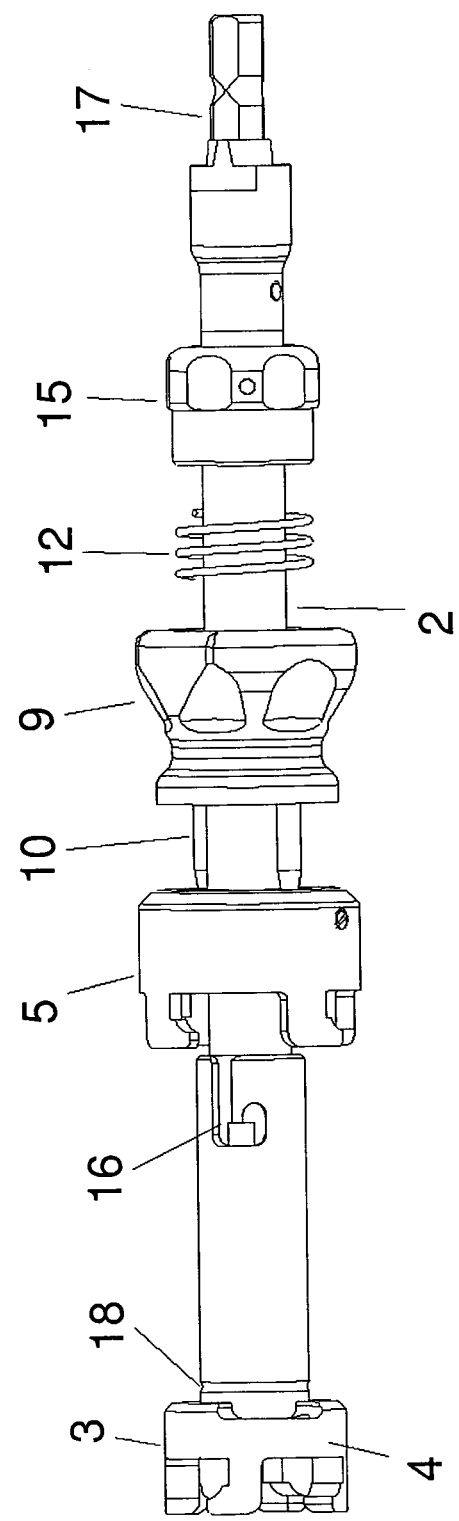
FIG. 4 shows the device of FIG. 1 with the component parts separated.

The outer ring 5 also contains spring plungers which locate on to a radial groove 18 machined fully around the diameter of the main body 2 (see FIG. 4). The purpose of these features is to prevent unintentional axial movement of the outer ring 5.

Once the inner ring 4 and the outer ring 5 are in the closed position, a securing block 9 is used to prevent the outer ring 5 from rotating relative to the inner ring 4 which may result in the cutting tool disengaging from the device 1. The securing block 9 slides axially down the main body 2, and has two tapered pins 10 protruding from it (see FIGS. 1 and 4). The tapered pins 10 locate through corresponding holes 11 in both the inner ring 4 and the outer ring 5. The action of the taper ensures that the assembly remains tightly secured to the modular connection.

In order to maintain tension in the system, a compression spring 12 and a bayonet release ring 15 are positioned behind the securing block 9, the bayonet release ring being releasably connectable with a J slot 16 disposed in main body 2 (see FIG. 4).

In order to release an instrument from the device 1 it is necessary to retract the securing block 9 axially back along the main body 2 and then rotate it clockwise. The design of the device 1 is such that by doing this the tapered pins 10 will still be located within the outer ring 5 and will cause the modular connection to open.

Figure 3:
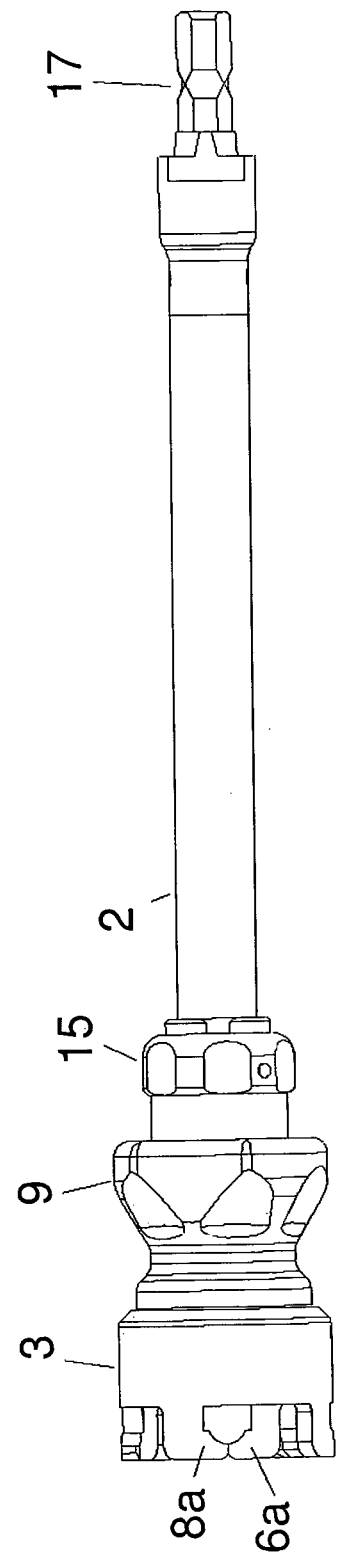
FIG. 3 is a side profile view of the device of FIG. 1.

As shown in FIGS. 3 and 4, the proximal end of the main body 2 has a second connector 17 for connecting the device 1 to a driver (not shown).

To allow for easy cleaning of the device, the bayonet release ring 15 can be disengaged from the J slot 16. By doing this all the components are free to move along the main body 2 of the device 1. However, second connector 17 prevents the components from coming fully off of the main body 2.

Figure 9:
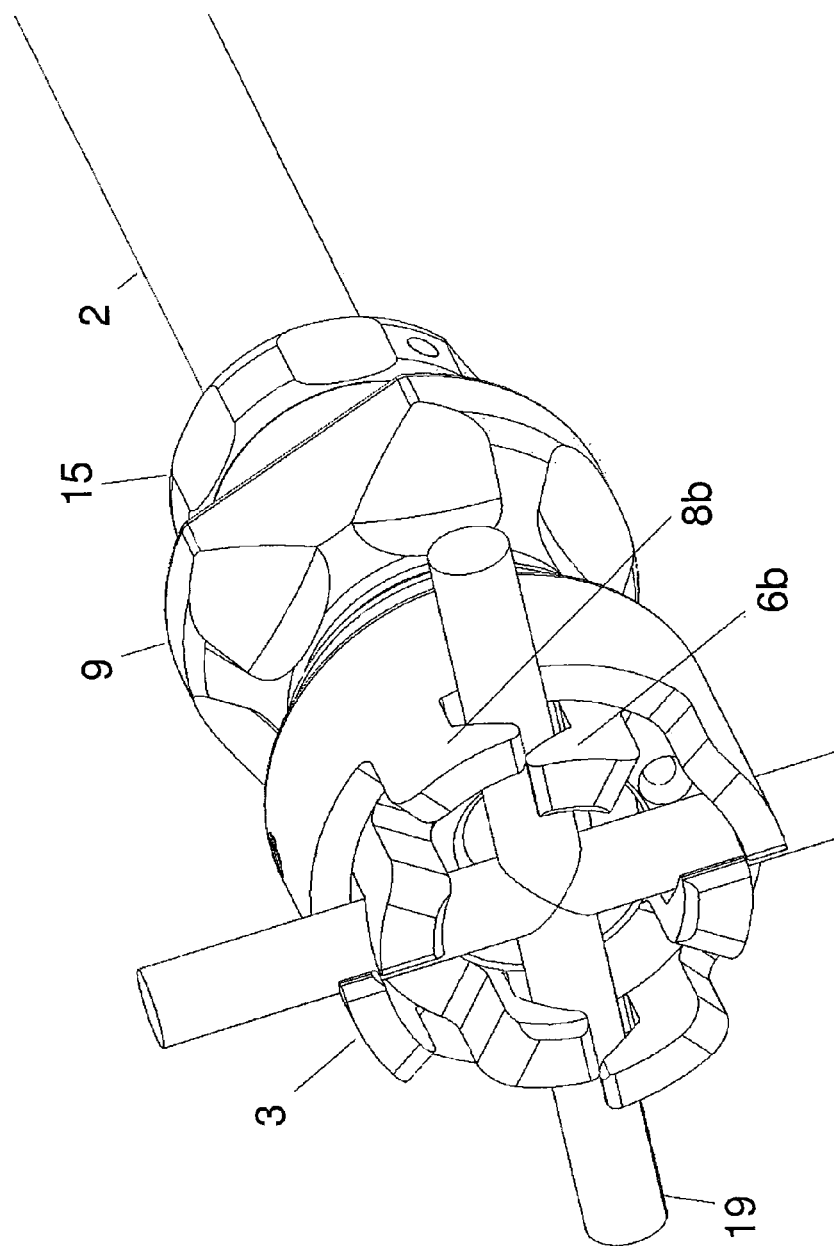
FIG. 9 shows the device of FIG. 7 connected to a crucifix connector.
Figure 10:
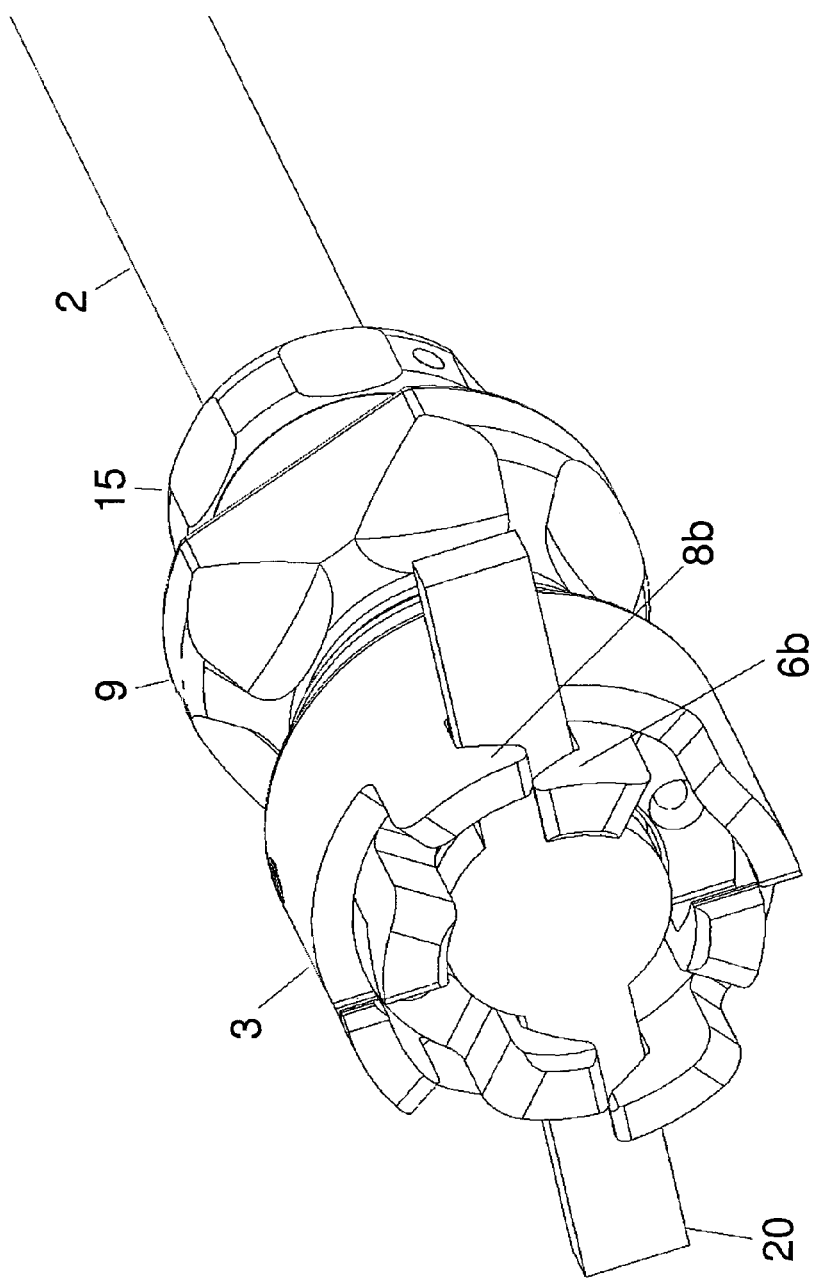
FIG. 10 shows the device of FIG. 7 connected to a bridge-back connector.

FIGS. 7 to 10 show the distal end of a device according to another embodiment of the present invention in the closed position. The device shown in FIGS. 7 to 10 has the same features as the device shown in FIGS. 1 to 6, with the exception that the tapered catches 6b, 8b are shaped with a straight taper such that they correspond to both the round cross-sectional profile of the crucifix connection 19 (see FIG. 9) and the rectangular profile of the bridge-back connection 20 (see FIG. 10). The device of FIGS. 7 to 10 therefore still enables engagement with either type of standard connection. As shown in FIGS. 9 and 10, the tapered catches 6b, 8b engage at different points with the connection depending on whether it is a crucifix connection 19 or a bridge-back connection 20. In addition, the device of FIGS. 7 to 10 also enables engagement with a plurality of other types of connections having different shapes. For example, n-sided connections where n is 3 or more.

An advantage of devices according to the present invention is that they allow both standard types of modular connection to attach to a single device. Devices according to the present invention also allow different, non-standard types of modular connection to attach to a single device.

Another advantage of devices according to the present invention is that they provide a more secure connection than known bayonet type devices. This is due to the larger area over which the design supports the modular connection. It is also due to the 'clamping' action resulting from the tapered pins on the securing block.

What is claimed is:

1. A device for connecting an instrument to a driver, the device comprising:
    a main body extending along a longitudinal central axis;
    a first connector having at least two protrusions connectable to the instrument;
    a mechanism for moving the protrusions between a connected and a disconnected position; and
    a second connector for connecting the device to the driver; and
    wherein the mechanism rotates the protrusions relative to one another about the longitudinal central axis of the main body between the connected and disconnected positions, wherein an adjacent pair of the protrusions together define a cavity in the connected position that is sized and shaped to receive a portion of the instrument to connect the device to the instrument, and wherein the adjacent protrusions each include a cut-out feature defining a recess whereby the adjacent protrusions define opposed recesses that together define the cavity.

2. A device according to claim 1, wherein the protrusions of the device connect to the instrument such that the instrument is clamped by the device.

3. A device according to claim 1, wherein the mechanism rotates the protrusions independently of each another about the longitudinal central axis of the main body between the connected and disconnected positions.

4. A device according to claim 1, wherein the mechanism rotates the protrusions in opposite directions about the longitudinal central axis of the main body between the connected and disconnected positions.

5. A device according to claim 1, wherein at least one protrusion is shaped so that it engages with a corresponding feature on the instrument.

6. A device according to claim 1, wherein at least one protrusion is in the form of a catch.

7. A device according to claim 1, wherein the instrument has at least one arm for connecting with the protrusions of the device.

8. A device according to claim 7, wherein the at least one arm is circular in cross-section.

9. A device according to claim 7, wherein the at least one arm is n-sided, and wherein n is 3 or more.

10. A device according to claim 9, wherein the at east one arm is rectangular in cross-section.

11. A device according to claim 1, wherein the first connector is disposed at a distal end of the main body and the second connector is disposed at a proximal end of the main body.

12. A device according to claim 1, wherein the instrument is a cutting tool.

13. A device according to claim 1, wherein the driver is a rotary drive source.

14. A device according to claim 1, wherein the cavity includes a first portion having a rectangular-shaped profile; and
wherein the cavity includes a second portion having a tapered profile.

15. A device according to claim 14, wherein the tapered profile of the second portion of the cavity comprises either a rounded configuration or a straight taper configuration.

16. A device according to claim 14, wherein the rectangular-shaped profile of the first portion of the cavity is defined by a pair of parallel side walls; and
wherein the tapered profile of the second portion of the cavity is defined by a pair of tapering side walls that inwardly taper toward one another.

17. A device according to claim 1, wherein the first connector comprises first and second concentric rings, the first concentric ring defining a first of the protrusions, the second concentric ring defining a second of the protrusions, and wherein rotation of the first concentric ring relative to the second concentric ring about the longitudinal central axis of the main body moves the protrusions between the connected position and the disconnected position.

18. A device according to claim 1, wherein the first connector defines at least two of the cavities in the connected position that are sized and shaped to receive corresponding portions of the instrument to connect the device to the instrument.

19. A device according to claim 18, wherein the at least two cavities are positioned opposite one another relative to the longitudinal central axis of the main body.

20. A device according to claim 1, wherein the first connector defines four of the cavities in the connected position that are sized and shaped to receive corresponding portions of the instrument to connect the device to the instrument, and wherein the four cavities are equally spaced about the longitudinal central axis of the main body.

21. A method of connecting an instrument to a driver, the method comprising:
providing an instrument;
providing a driver;
providing a device including a main body extending along a longitudinal central axis, the device including a first connector having at least two protrusions, a mechanism for moving the protrusions between a connected position and a disconnected position, and a second connector;
connecting the first connector to the instrument and connecting the second connector to the driver; and
rotatably moving the protrusions independently of one another about the longitudinal central axis of the main body between the connected and disconnected positions, wherein an adjacent pair of the protrusions together define a cavity in the connected position that is sized and shaped to receive a portion of the instrument to connect the device to the instrument, and wherein the adjacent protrusions each include a cut-out feature defining a recess whereby the adjacent protrusions define opposed recesses that together define the cavity.

22. The method according to claim 21, further comprising the step of rotatably moving the protrusions in opposite directions about the longitudinal central axis of the main body between the connected and disconnected positions.

23. The method according to claim 21, wherein the cavity includes a first portion having a rectangular-shaped profile and a second portion having a tapered profile.

24. The method according to claim 21, wherein the first connector comprises first and second concentric rings, the first concentric ring defining a first of the protrusions, the second concentric ring defining a second of the protrusions, and wherein rotation of the first concentric ring relative to the second concentric ring about the longitudinal central axis of the main body moves the protrusions between the connected position and the disconnected position.

* * * * *